(12) United States Patent
Hu et al.

(10) Patent No.: US 6,203,984 B1
(45) Date of Patent: Mar. 20, 2001

(54) PROPORTIONAL AMPLIFICATION OF MRNA FROM A LINEAR TEMPLATE IN VITRO

(75) Inventors: Qianjin Hu, Castro Valley; Allan Peng, Palo Alto, both of CA (US)

(73) Assignee: Pacron, Inc., San Leandro, CA (US)

( * ) Notice: Subject to any disclaimer, the term of this patent is extended or adjusted under 35 U.S.C. 154(b) by 0 days.

(21) Appl. No.: 09/109,377

(22) Filed: Jul. 2, 1998

(51) Int. Cl.[7] ............................................ C12Q 1/68
(52) U.S. Cl. ..................... 435/6; 435/69.1; 435/91.1; 435/91.2; 435/320.1

(58) Field of Search ................... 435/6, 69.1, 320.1, 435/91.1, 91.2

Primary Examiner—Ardin H. Marschel
(74) Attorney, Agent, or Firm—Morrison & Foerster LLP

(57) ABSTRACT

The invention concerns polynucleotide compositions and methods for copying and amplifying mRNA, and provides for a method of making a linear cDNA or cRNA library based on original mRNA templates. The linear polynucleotides have the advantage of being more completely representative of full length mRNA transcripts than previously possible, and the linear libraries constructed by these methods represent relative abundances of the original transcripts in the original population of mRNA more accurately than previously possible.

17 Claims, No Drawings

SEQUENCE LISTING

<160> NUMBER OF SEQ ID NOS: 5

<210> SEQ ID NO 1
<211> LENGTH: 62
<212> TYPE: DNA
<213> ORGANISM: Unknown
<220> FEATURE:
<223> OTHER INFORMATION: Primer

<400> SEQUENCE: 1
ctcgtattct atagtgtcac ctaaatggcc tatatggcct tttttttttt tttttttttt     60
tt                                                                    62

<210> SEQ ID NO 2
<211> LENGTH: 18
<212> TYPE: DNA
<213> ORGANISM: Unknown
<220> FEATURE:
<223> OTHER INFORMATION: Primer

<400> SEQUENCE: 2
atttaggtga cactatag                                                   18

<210> SEQ ID NO 3
<211> LENGTH: 19
<212> TYPE: DNA
<213> ORGANISM: Unknown
<220> FEATURE:
<223> OTHER INFORMATION: Primer

<400> SEQUENCE: 3
tctatagtgt cacctaaat                                                  19

<210> SEQ ID NO 4
<211> LENGTH: 13
<212> TYPE: DNA
<213> ORGANISM: Unknown
<220> FEATURE:
<223> OTHER INFORMATION: Primer

<400> SEQUENCE: 4
ggcctatatg gcc                                                        13

<210> SEQ ID NO 5
<211> LENGTH: 28
<212> TYPE: DNA
<213> ORGANISM: Unknown
<220> FEATURE:
<223> OTHER INFORMATION: Primer
<220> FEATURE:
<221> NAME/KEY: variation
<222> LOCATION: (28)...(28)
<223> OTHER INFORMATION: n = any nucleotide
<220> FEATURE:
<221> NAME/KEY: variation
<222> LOCATION: (26)...(26)
<223> OTHER INFORMATION: s = g or c
<220> FEATURE:
<221> NAME/KEY: variation
<222> LOCATION: (27)...(27)
<223> OTHER INFORMATION: d = a or g or t

<400> SEQUENCE: 5
gaagatctgg cccatatggc caggasdn                                        28

PROPORTIONAL AMPLIFICATION OF MRNA FROM A LINEAR TEMPLATE IN VITRO

FIELD OF THE INVENTION

The invention relates to compositions and methods for amplification of mRNA.

BACKGROUND

Standard procedures for copying mRNA and amplifying mRNA exist in the art, and are the foundation of much of the recent work and advancements in molecular biology. Copying and amplifying mRNA, and using these copies to generate a library of polynucleotides that represent the original mRNA provides researchers with templates for cloning and analysis of the original transcripts. Knowledge of the original transcripts allows analysis and manipulation of the expression products of the genes upon which the transcripts are based. Any tools that can further the usefulness and accuracy of methods of copying and amplifying mRNA are extremely useful and sought after in the fields of molecular biology and functional genomics.

SUMMARY

The invention is a single stranded DNA molecule comprising in 5' to 3' order: (a) a promoter, (b) a restriction endonuclease cleavage site, and (c) an oligonucleotide dT sequence having at least 10 dTs, wherein the promoter is oriented so that it initiates transcription towards the 5' end, and further wherein between 0 and 100 nucleotides are between each of elements (a), (b), and (c). This molecule can further comprise additional nucleotides 3' of the oligonucleotide dT sequence, and these additional nucleotides can comprise a first strand cDNA sequence. The molecule can be circular, or a linear catenate of at least two series of elements (a), (b), (c), and (d). These molecules can further comprise a second strand complementary to and hydrogen-bonded to the single stranded DNA molecule. Consistent with the composition of the invention is a method of forming a template for producing mRNA comprising cleaving the DNA molecule with a second strand complementary to it with the restriction endonuclease to form a DNA template having a promoter upstream of a coding sequence oriented to transcribe downstream.

Similarly, for the purpose of making antisense copies, the invention is also a single stranded DNA molecule comprising in 5' to 3' order: (a) a restriction endonuclease cleavage site, (b) a promoter, and (c) an oligonucleotide dT sequence having at least 10 dTs, wherein the promoter is oriented so that it initiates transcription towards the 3' end, and further wherein between 0 and 100 nucleotides are between each of elements (a), (b), and (c). For making antisense polynucleotides, the permutations described above also apply.

The invention includes a method of making cDNA comprising (a) incubating mRNA with reverse transcriptase, deoxyribonucleotide triphosphates and a first oligonucleotide primer comprising in a 5' to 3' orientation (i) a promoter, (ii) a restriction endonuclease cleavage site, and (iii) an oligonucleotide dT sequence having at least 10 dTs, wherein the promoter is oriented so that it initiates transcription towards the 5' end, and further wherein between 0 and 100 nucleotides are between each of elements (i), (ii), and (iii) to form first strand cDNA comprising at its 5' end the first oligonucleotide primer, (b) removing the mRNA from the first strand cDNA, (c) phosphorylating the 5' end of the first strand cDNA, (d) ligating the phosphorylated first strand cDNA with ligase to form a linear catenate of first strand cDNA or a circular first strand cDNA, (e) incubating the linear catenate or circular cDNA with a DNA polymerase, deoxyribonucleotidetriphosphates, and a second oligonucleotide primer which is complementary to at least 12 nucleotides of the first oligonucleotide primer to form a double stranded linear catenate or circular cDNA, (f) cleaving the double stranded linear catenate or circular cDNA with the restriction endonuclease to form a double stranded template having the promoter upstream of the cDNA, oriented to transcribe downstream. This method can further comprise step (g) transcribing the double stranded template of step (f) with RNA polymerase and nucleotide-triphosphates to form single stranded cRNA. Still further the method can comprise step (h) amplifying the double stranded template of step (f) with DNA polymerase, deoxyribonucleotidetriphosphates, a third oligonucleotide primer complementary to at least 12 nucleotides of the 3' end of a first strand of the cDNA, and a fourth oligonucleotide primer complementary to at least 12 nucleotides of the 3' end of the second strand. Still further the method can comprise step (i) transcribing and translating in vitro the double stranded template of step (f) to make a polypeptide encoded by the cDNA.

Another method of the invention is a method of making cDNA comprising, (a) decapping an mRNA, (b) ligating a first oligonucleotide primer comprising a promoter to a 5' end of the mRNA molecule to form an RNA template, wherein the promoter is oriented to transcribe towards the 3' end, (c) reverse transcribing the RNA template of step (b) with reverse transcriptase, deoxyribonucleotidetriphosphates and a second oligonucleotide primer comprising an oligonucleotide dT sequence of at least 10 dTs, and an additional nucleotide sequence 5' of the oligonucleotide dT sequence, to form first strand cDNA, (d) removing the mRNA from the first strand cDNA, (e) incubating the first strand cDNA, a DNA polymerase, deoxyribonucleotidetriphosphates, and a third oligonucleotide primer comprising at least 12 nucleotides of the first primer sequence, to form double stranded cDNA.

Further the invention includes a method of substractive hybridization identifying mRNA transcripts that are not common to two populations of mRNA comprising, (a) reverse transcribing a first mRNA population with reverse transcriptase, deoxyribonucleotidetriphosphates, and a first nucleotide primer comprising in 5' to 3' order: (i) a promoter, (ii) a restriction endonuclease cleavage site, and (iii) an oligonucleotide dT sequence having at least 10 dTs, wherein the promoter is oriented so that it initiates transcription towards the 5' end, and further wherein between 0 and 100 nucleotides are between each of elements (i), (ii), and (ii), to form first strand cDNA comprising at a 5' end the first primer sequence, (b) removing the mRNA from the first strand cDNA, (c) hybridizing the first strand cDNA of step (b) to a second mRNA population to form a composition comprising cDNA:mRNA hybrids and nonhybridized first strand cDNA, (d) eliminating the cDNA:mRNA hybrids from the composition, (e) ligating the composition comprising non-hybridized first strand cDNA with ligase to form linear catenates or circular first strand cDNA, (f) incubating the first strand linear catenates or circular cDNA with DNA polymerase, deoxyribonucleotidetriphosphates, and a second oligonucleotide primer complementary to at least 12 nucleotides of the first primer sequence to form double stranded linear catenates or circular cDNA, (g) cleaving the double stranded linear catenates or circular cDNA with the restriction endonuclease to form cDNA having a promoter upstream of a coding sequence oriented to transcribe downstream representing mRNA molecules which are not common to the two mRNA populations.

The invention also includes a method of reducing the quantity of a select mRNA present in a population of mRNA comprising, (a) reverse transcribing a first mRNA population with reverse transcriptase, deoxyribonucleotidetriphosphates, and a first nucleotide primer comprising in 5' to 3' order: (i) a promoter, (ii) a restriction endonuclease cleavage site, and (iii) an oligonucleotide dT sequence having at least 10 dTs, wherein the promoter sequence is oriented so that it initiates transcription towards the 5' end, and further wherein between 0 and 100 nucleotides are between each of elements (i), (ii), and (iii), to form first strand cDNA comprising at a 5' end the first primer sequence, (b) removing the mRNA from the first strand cDNA, (c) hybridizing for a sufficient period of time the first strand cDNA of step (a) to the mRNA of step (a) to form a composition comprising cDNA:mRNA hybrids of some but not all of the cDNA and mRNA pairs that can hybridize, (d) eliminating the cDNA:mRNA hybrids that are formed from the composition., (e) ligating the composition comprising nonhybridized first strand cDNA with ligase to form linear catenates or circular first strand cDNA, (f) incubating the first strand linear catenates or circular cDNA with DNA polymerase, deoxyribonucleotidetriphosphates, and a second oligonucleotide primer complementary to at least 12 nucleotides of the first primer sequence to form double stranded linear catenates or circular cDNA, (g) cleaving the double stranded linear catenates or circular cDNA with the restriction endonuclease to form cDNA having a promoter upstream of a coding sequence, oriented to transcribe downstream, representing mRNA molecules that are not common to the two mRNA populations.

DETAILED DESCRIPTION

The invention is a method of making a copy of an mRNA. The copy can be cDNA or cRNA. The invention is also a method of amplifying an mRNA, or a population of mRNA. The particular advantages of the invention are that the methods provide more full length copies of the mRNA than previously achievable, and provide amplification in direct proportion to the representation in the original mRNA population. With respect to the latter advantage, this means that the amplified mRNA population is not distorted or disproportional to the original mRNA representation, but rather proceeds in a nearly linear fashion. The resulting polynucleotide copies of the mRNA more accurately represent the original population. For example, where 5 mRNA copies of a particular coding sequence are present in the population, where the entire population is amplified to about 5 times its original size, there would be 25 copies of that particular mRNA template as cDNA or cRNA copies.

The invention includes a composition that is a primer for synthesis of first strand cDNA. The primer is used to facilitate the methods of the invention. The basic elements of the primer provide that the template created to make the copies of mRNA can be linear polynucleotides and that the copying and amplification proceeds in vitro. In addition, the invention provides that cRNA can be made from the mRNA in vitro and that cDNA templates are made from the original mRNA. The invention also provides that the cDNA can be cloned into vectors for sequencing, cloned into expression vectors for expression, expressed using an additional regulatory sequences placed in the primer (in addition to the basic elements of the primer) for expressing the coding sequence in an appropriate expression system, and also that the DNA can be in vitro transcribed and translated. The manipulations possible with the linear template cDNA copies of the mRNA can be achieved in systems such as, for example, all eukaryotic or prokaryotic systems desired. Within those large categories, the systems can include fungi, mammalian, insect, amphibian, bacterial or other expression systems. The manipulations that can be accomplished include in vitro transcription, in vitro translation, or other molecular biology manipulations or processes without or within cells. In short, the invention, both the compositions and methods, provide the opportunity for the user to generate a cDNA or cRNA library of linear polynucleotides that are more nearly proportional amplification products of the original mRNA population. These polynucleotides are more completely full length copies of the original mRNA. The polynucleotides have the potential for further manipulations including, for example, in vitro transcription to cRNA from the linear nucleotide template (from the linear double stranded cDNA template), and in vitro translation (after in vitro transcription) for such studies as 2D gel analysis either from the linear template or after placement into another vector system. The polynucleotides can be expressed in any type of cell system available either from the linear template or after placement into an appropriate expression vector. The polynucleotides can be sequenced by any method possible either from the linear template or after placement into a sequencing vector. In addition, further amplification by the present method or by other standard methods such as for example by polymerase chain reaction (PCR) can take place.

The invention also provides a way to perform substractive hybridization of copies of the mRNA species so that cDNA copies of the mRNA to which an inquiry is not directed can be excluded from the copies of the population. The invention also provides a way to equalize or normalize the copies of the mRNA species in a library generated from a population of mRNA, so that the relative amounts of cDNA copies of the mRNA are more equal for a given template in a given population of mRNA than they would be without the equalization procedure. As such, the inventions present powerful tools in molecular biology for analysis of a population of mRNA, for comparative purposes, direct functional analysis of expression or transcription products of various members of the population, and for other perhaps as yet not fully developed uses in the field of molecular biology and functional genomics.

The primers of the invention are DNA molecules capable of hybridizing to an mRNA molecule for synthesis of a first strand cDNA molecule. One primer for making a template for making mRNA is single stranded and has the following elements in 5' to 3' order: a promoter, a restriction endonuclease cleavage site, and an oligonucleotide dT sequence. The promoter is oriented so that it initiates transcription towards the 5' end.

The promoter sequence can be any promoter sequence capable of initiating transcription of a coding sequence in an in vitro context. Thus, the promoter will generally need to have available the RNA polymerase enzyme appropriate for in vitro transcription from that promoter sequence. The promoter can be, for example, a T7, T3 or SP6 promoter, (or any other promoter for which is available the enzyme for in vitro transcription) and these promoters are used in conjunction with the corresponding T7, T3, and SP6 RNA polymerases for making the cRNA from a double stranded linear cDNA template in vitro. The orientation of the promoter in the primer should be that the promoter sequence is oriented so that it initiates transcription towards the 5' end. In the double stranded cDNA the promoter is upstream of a coding sequence oriented to transcribe downstream.

Although not necessary for the basic method of the invention, other promoter sequences, such as promoters that function in eukaryotic cell systems, such as yeast, mammalian, or insect promoters can be included in the primer sequence for facilitating expression in these cell systems later. These additional promoter sequences which are for expression or other purposes are generally distinguished from the promoter in the primer for the purpose of in vitro transcription.

The restriction endonuclease cleavage site is a nucleotide sequence of, for example, 4, 6, or 8 nucleotide bases that can be recognized and cleaved by a restriction endonuclease. The restriction enzyme can also recognize at one site and cut at a distant site, provided that the cutting leaves an intact and functioning promoter and a sufficient length of oligo dT sequence. In order to minimize the likelihood that the coding sequence of interest contains the same cleavage site as this element of the primer, rare cleavage sites are preferred, for example those having 8 or more nucleotides, although the invention can work perfectly well using a site with 4 bases, or 6 bases. One of the goals in selecting a restriction endonuclease would be to have the enzyme cut in primer at the restriction site, but not in the coding sequence. Restriction endonucleases that recognize sites having 8 bases include Sfi I, Not I, Asc I, Fse I, Pac I, Pme I, Sbf I, SgrA I, and Swa I, and in most circumstances the cleavage and recognition sites of these endonucleases and their corresponding restriction endonucleases are preferred for the invention.

The oligonucleotide dT sequence should have at least 10 dTs, and can have many more if desired. Thus, the oligonucleotide dT sequence can have from 10 to 100 dTs, 20 to 80 dTs, 30 to 70 dTs, 40 to 60 dTs, but most preferably in the range from 10 to 30 dTs. It does not compromise the invention to have an occasional dA, dC, or dG, or two or several of such non-dT nucleotides as part of the oligo dT sequence. Thus, the dT sequence need not be exclusively dTs, although at least 10 consecutive oligonucleotide dTs should be present in the sequence. For example, the sequence have 12 consecutive dTs followed by a dA, and a dG, have 5 consecutive dTs, followed by a dC and a dA, and 20 consecutive dTs followed by two dGs. Another example, might be 10 consecutive dTs, followed by a dG, followed by another 10 consecutive dTs, followed by 3 dGs, followed by 7 consecutive dTs, followed by a dA, a dC and 2 dGs, followed by 15 dTs.

In between these three basic elements of the primer can exist between 0 and 100 nucleotides, or more. Thus, between 0 and 100 nucleotides, or more, can exist between the promoter and the restriction endonuclease site that are neither part of the promoter, nor are they nucleotides that are part of the restriction endonuclease recognition and cleavage site. Also, in between the restriction endonuclease site and the sequence of oligonucleotide dTs can exist between 0 and 100 nucleotides, or more that are neither part of the restriction site nor part of the oligonucleotide dT sequence. There may be other purposes of structure or function assigned to these spacer nucleotides if they are present in the design of the primer, or they may act simply as spacer nucleotides. Particularly in the space between the oligonucleotide dT sequence and the restriction endonuclease cleavage sequence, other nucleotides may be placed and may serve a later function in the usefulness of the template mRNA or DNA that is made. For example, an expression promoter can be included in the sequence for expressing a protein from the coding sequence in a cell system as a later manipulation.

The primer just described can be used to generate linear first strand cDNA molecule from an mRNA template, so that the resulting molecule has, in the 5' to 3' orientation, the primer followed by a sequence of additional nucleotides complementary to the mRNA template. The sequence of additional nucleotides can be for example, a coding sequence of a gene, or part of a gene. The first strand cDNA molecule is single stranded.

The first strand cDNA molecule can be circularized in the presence of T4 RNA ligase (commercially available) or other ligase capable of ligating single stranded nucleotide sequences. The resulting circular molecule is also contemplated by the invention. The circular molecule can be single or double stranded. Additionally, the first strand cDNA molecule can be ligated to other linear molecules of similar structure to form a linear catenate. These concatemers can be single stranded or double stranded. The double stranded molecules can be made from the single stranded catenates and the single stranded circular molecules by incubating in the presence of DNA polymerase, a primer of from 15 to 50 nucleotides, or about 20 to about 40 nucleotides, or about 30 nucleotides, most preferably about 18 to 25 nucleotides complementary to a portion of the primer sequence, for example a portion of the promoter sequence of the primer described above, and reagents for a standard DNA polymerization reaction under the appropriate reaction conditions. Both the ligation and the polymerization can be conducted as described in Sambrook et al, Cold Springs Harbor Laboratory Press, Cold Springs Harbor, N.Y. 1989, or as described by the commercial manufacturer of the enzymes. Circularization versus catenation is generally controlled by the concentration of the substrate single stranded molecules. More dilute conditions favor circularization. Variations on the primer sequence include a variation of the primer described above useful for making antisense molecules from mRNA. These primers have in 5' to 3' order: a restriction endonuclease cleavage site as described above, a promoter as described oriented so that it initiates transcription towards the 3' end, and an oligonucleotide dT sequence also as described above. Also as described above, the primer can have between 0 and 100 nucleotides, or more, between each of the elements (the cleavage site, the promoter and the oligo dT sequence). First strand cDNA including this primer at the 5' end can also be circularized and can form linear catenates, both of which can be single or double stranded. In the double stranded cDNA the promoter is downstream of a coding sequence, oriented to transcribe upstream. Thus antisense cDNA is formed from DNA synthesis with this primer. Thus an antisense cDNA library can be formed. Antisense DNA has many uses, among them that it can be used to probe Northern blots, or for other uses such as antisense gene therapy.

The invention includes several methods based on the basic primers described. The reaction steps used to perform these methods are all standard procedures such as described in Sambrook et al, Cold Springs Harbor Laboratory Press, Cold Springs Harbor, N.Y. 1989.

The first method employs the first primer describe above. This method is a method of making a template for producing copies of mRNA. The double stranded circularized or linear catenate cDNA molecule described above, having the first primer sequence (promoter oriented 3' to 5', restriction endonuclease site, and oligonucleotide dT sequence) and a sequence of additional nucleotides 3' of the oligonucleotide dTs, is cleaved with the restriction endonuclease specific for the restriction site. From this cleavage a double stranded molecule is formed that has a promoter upstream of a coding sequence, oriented so that it transcribes downstream, the additional nucleotide sequence, for example a coding sequence, an oligo dA sequence, and any other sequence (from 0 to 100 bases, or more) that may have been inserted in the original primer.

The DNA molecule so created is double stranded cDNA and can be a component of a linear cDNA library, can be placed in another vector to make an expression library, or can be used in the presence of the RNA polymerase that corresponds to the promoter sequence in the primer to generate in vitro cRNA template copies of the original mRNA (a cRNA library). The cDNA templates can be amplified in the presence of DNA polymerase, or can be sequenced using primers appropriate to its structure by standard sequencing methods. The linear cDNA can also be ligated into other vectors for other uses, including to express the coding sequence. The already amplified linear cDNA can also be further amplified using polymerase chain reaction (PCR), using standard procedures for performing PCR. In greater detail, the method of the invention for making template copies of mRNA includes incubating mRNA with a reverse transcriptase enzyme, deoxyribonucleotide triphosphates, and the primer (in 5' to 3' orientation: a promoter, restriction endonuclease cleavage site, and an oligonucleotide dT sequence, with the promoter oriented so that it initiates transcription towards the 5' end; the primer also having optionally between 0 and 100 nucleotides, or more, between the promoter and cleavage site, the cleavage site and the oligonucleotide dT sequence, or both). The appropriate buffer and reaction conditions that are standard in the art for reverse transcription reactions are used. The molecule that results is a cDNA molecule having from 5' to 3' the primer sequence and the additional nucleotides. The double stranded cDNA has a promoter upstream of a coding sequence, followed by the oligo dA, where the promoter is oriented to transcribe downstream.

The mRNA and any other RNA present is then removed from the reaction mixture. This can be accomplished by any method available to remove RNA from a reaction, including an RNA separation column, hydrolysis with NaOH, or digestion with an RNase enzyme. The remaining first strand cDNA is then ligated with a ligase, for example RNA ligase. From the ligation circularized cDNA molecules, and linear catenates of repeating units of cDNA molecules are formed. The catenates have at least two repeating units. It is also conceivable that a small catenate could get circularized. The circular or linear molecules are then used as templates for second strand synthesis in the presence of reaction components including a DNA polymerase, all four deoxyribonucleotidetriphosphates, and a second oligonucleotide primer. The second oligonucleotide primer should have at least 12 nucleotides in common with the first primer, and preferably at least 18 or 20 nucleotides. From the second strand synthesis reaction, double stranded circularized or linearized cDNA molecules are formed. The various double stranded cDNA molecules can be cleaved with the restriction endonuclease enzyme specific for the cleavage site. The cleavage reaction is conducted as is standard in the art for cleaving double stranded DNA to completion, and usually includes an incubation period at specified temperature.

The linear double stranded cDNA molecules resulting from the incubation with the restriction endonuclease cleavage enzyme have the promoter upstream of a coding sequence, oriented to transcribe downstream.

Further manipulations that are possible include in vitro transcription using the promoter and its corresponding RNA polymerase enzyme under standard reaction conditions for this procedure. Linear cRNA, and library of linear cRNA, results from the in vitro transcription procedure. In this way, the original mRNA is further amplified, with the advantage of an approximately linear amplification so that the original population of mRNA is proportionally represented in the copies of cRNA that result.

The double stranded cDNA template is in vitro transcribed with RNA polymerase and all four ribonucleotidetriphosphates to form single stranded cRNA. This process is accomplished in vitro. The promoter corresponds to the RNA polymerase selected for facilitating the in vitro transcription of the linear cDNA to form linear cRNA.

The double stranded cDNA template can also optionally be amplified in the presence of DNA polymerase, deoxyribonucleotidetriphosphates, a third oligonucleotide primer complementary to at least 12 nucleotides at the 5' end of the cDNA template, and a fourth oligonucleotide primer complementary to at least 12 nucleotides of the oligonucleotide dT sequence of the second strand. Alternatively, the third primer is complementary to 12 nucleotides of the antisense strand of the promoter sequence, and the fourth primer is complementary to 12 nucleotides of the oligo dA sequence of the sense strand. The amplification can be accomplished by PCR under standard conditions using Taq DNA polymerase.

The linear double stranded cDNA template can also be transcribed and translated in vitro using procedures standard in the art to make a polypeptide encoded by the cDNA sequence. Such procedures typically employ rabbit reticulocyte lysates or wheat germ lysates. The resulting polypeptides can be used for 2D gel analysis of the expression products, polypeptide sequencing and other analysis or manipulations that are desired.

Another method employs a primer described above for making antisense copies of the original mRNA population. The double stranded circularized or linear catenate cDNA molecule described above, having the primer sequence (restriction endonuclease site, promoter oriented to initiate transcription towards the 3' end, restriction endonuclease site, and oligonucleotide dT sequence) and a sequence of additional nucleotides 3' of the oligonucleotide dTs, is cleaved with the restriction endonuclease specific for the restriction site. From this cleavage is a double stranded molecule is formed that has a promoter downstream of a coding sequence, where the promoter is oriented to transcribe upstream, and thus to make antisense cDNA. From this DNA template, after the ligation and cleavage as described above, a cDNA or cRNA antisense molecule or library can be made. Antisense cRNA is useful as probes in many contexts, including Northern blots, and functional genomics analysis. The cDNA templates can also be amplified in the presence of DNA polymerase, or can be sequenced using primers appropriate to its structure, using standard nucleotide sequencing methods. The cDNA can be also be ligated into vectors. Antisense cDNA is useful for probing Northern blots and in antisense gene therapy.

In greater detail, the method of the invention for making cDNA includes incubating mRNA with reverse transcriptase enzyme, deoxyribonucleotide triphosphates, and the primer (in 5' to 3' orientation: restriction endonuclease cleavage site, a promoter, and an oligonucleotide dT sequence, with the promoter oriented so that it initiates transcription towards the 3' end; the primer also having optionally between 0 and 100 nucleotides, or more, between the cleavage site, and the promoter and the oligonucleotide dT sequence, or both). The appropriate buffer and reaction conditions that are standard in the art for reverse transcription reactions should be used. The molecule that results is a first strand cDNA molecule.

The mRNA and any other RNA present is then removed from the reaction mixture as described above. The remaining first strand cDNA is then ligated with a ligase, for example RNA ligase. From the ligation are formed circularized cDNA molecules, and linear catenates of repeating units of cDNA molecules. The circular or linear molecules are then polymerized in the presence of reaction components including a cDNA polymerase, deoxyribonucleotidetriphosphates, and a second oligonucleotide primer. The second oligonucleotide primer should have at least 12 nucleotides in common with the first primer, and preferably at least 18 or 20 nucleotides. From the polymerization, double stranded circularized or linearized cDNA molecules are formed. The various double stranded cDNA molecules in the solution can be cleaved with the restriction endonuclease enzyme specific for the cleavage site. The reaction is conducted as is standard in the art for cleaving double stranded DNA to completion, and usually includes an incubation period at specified temperature.

The double stranded cDNA molecules resulting from the incubation with the restriction endonuclease cleavage enzyme have a promoter downstream of a coding sequence, oriented to transcribe upstream. In this method, when the promoter transcribes, an antisense sequence results.

Further manipulations can include taking the double stranded cDNA template just described and transcribing it with RNA polymerase and nucleotidetriphosphates forming single stranded antisense cRNA.

The double stranded cDNA template can also be amplified in the presence of DNA polymerase, deoxyribonucleotidetriphosphates, and appropriate primers as described above. The antisense cDNA molecules can be used as probes for Northern blots, or in antisense gene therapy, among other uses.

An alternative method of the invention for making cDNA is to isolate mRNA from cells or tissue mRNA molecules comprise a nucleotide sequence ending in a poly A tail, and are single stranded. The mRNA must be decapped which can be accomplished by techniques standard in the art. For example enzymes and reagents can be purchased commercially from Epicentre Technologies in Madison, Wis., including tobacco acid pyrophosphatase for decapping RNA. A first primer is ligated to the 5' end of the mRNA with a ligase capable of ligating single stranded RNA to single stranded DNA, for example T4 RNA ligase. Any ligase that can ligate DNA to RNA can be used. The first primer comprises a promoter sequence oriented to transcribe towards the 3' end of the mRNA. The promoter sequence can be any promoter sequence capable of facilitating in vitro transcription, including, for example a T7, T3, or SP6 promoter sequence. Generally, these promoters will be paired with the appropriate RNA polymerase enzyme, which accomplishes the in vitro transcription. A second primer having in 5' to 3' order from 0 to 100 nucleotides, or more, and an oligonucleotide dT sequence of at least 10 consecutive dTs is added to the reaction with reverse transcriptase enzyme and appropriate buffers and deoxyribonucleotidetriphosphates to achieve reverse transcription of the sense mRNA strand. The mRNA is then removed by any appropriate means, including, for example by addition of NaOH or RNase. At this stage single stranded cDNA has been made and includes from 5' to 3' the second primer sequence, complementary sequence to the mRNA and first primer. The first primer, or at least a 12 nucleotide sequence of the first primer can then be used in the reaction to generate double stranded cDNA from the single stranded antisense strand, using DNA polymerase and deoxyribonucleotidetriphosphates. From the double stranded cDNA, cRNA can be generated in the presence of RNA polymerase in an in vitro reaction. The RNA polymerase will be appropriate for the promoter sequence. For example, where a T7 promoter is used, a T7 RNA polymerase is used to catalyze the in vitro transcription reaction. Single-stranded cRNA representing copies and an amplification of the original mRNA population results. The cDNA can also be amplified using a 5' and a 3' primer, each complementary to a different strand, a DNA polymerase, for example Taq DNA polymerase, deoxyribonucleotidetriphosphates, and appropriate buffer and temperature conditions for a polymerase chain reaction (PCR). The cDNA can also be ligated into a vector for performing other manipulations, including expression, or other amplifications or analysis. From the linear double stranded cDNA the coding sequence can be in vitro transcribed and translated, and the resulting polypeptide can be used for 2D gel analysis, or other analytical, diagnostic, or therapeutic purposes. Vectors for expression can include any eukaryotic or bacterial expression vector, including mammalian, yeast, amphibian or insect expression vectors. The cDNA can be sequenced from the linear template, or placed in a sequencing vector.

The invention also includes a method of substractive hybridization. Substractive hybridization allows identification of mRNA transcripts that are not common to two populations of mRNA. For example, comparing mRNA transcripts from a normal and a tumor cell of the same tissue e.g., liver tissue and liver cancer tissue. The method includes reverse transcribing a first mRNA population with reverse transcriptase, deoxyribonucleotidetriphosphates, and a first nucleotide primer comprising in 5' to 3' order: (i) a promoter, (ii) a restriction endonuclease cleavage site, and (iii) an oligonucleotide dT sequence having at least 10 dTs, wherein the promoter sequence is oriented so that it initiates transcription towards the 5' end, and further wherein between 0 and 100 nucleotides, or more, are between each of elements (i), (ii), and (ii), to form first strand cDNA comprising at a 5' end the first primer sequence; removing the mRNA from the first strand cDNA, and hybridizing the first strand cDNA of that has been made from the first population of mRNA to another, second, population of mRNA The hybridization forms a composition comprising cDNA:mRNA hybrids and nonhybridized first strand cDNA. The cDNA:mRNA hybrids are eliminated from the composition by means standard in the art of molecular biology, including for example using an affinity column that retains the hybrids in the column and allows the non-hybridized molecules to pass through into an eluant. The hybrids can be eliminated from the composition using standard methods, including separation of single stranded DNA by Bio-Gel HTP hydroxyapatite, the reagents and protocol available from Bio-Gel, Hercules, CA. The remaining, nonhybridized single stranded first strand cDNA is phosphorylated by standard phosphorylation reaction, using, e.g., polynucleotide kinase and phosphates for generating phosphorylated 5' ends of the cDNA. The polynucleotide kinase can be, for example, T4 polynucleotide kinase. The phosphorylated single stranded cDNA is then treated with a single strand ligase, such as T4 RNA ligase, or other ligase capable of single stranded nucleotide ligation, and linear catenates and circular cDNA single stranded molecules are formed. A second strand complementary to the first strand of DNA is made by using the first strand DNA as a template with a primer that is complementary to a sequence on the primer originally used to make the first strand cDNA. The second primer need only be long enough to facilitate the polymerization, and accordingly can be at a minimum 12 bases long, optimally at least 18 bases long, and even longer. The second primer can be, for example, 18 bases corresponding to par of the sense sequence of the promoter. Where the first primer has the sequence of the promoter, the second primer is the sense sequence of a portion of the promoter sequence in the first primer. In the presence of DNA polymerase, and deoxyribonucleotidetriphosphates and appropriate buffers, the single stranded cDNA in linear catenates and circular forms are used as templates to form double stranded linear catenates and circular cDNA. Using a standard restriction endonuclease reaction, the double stranded molecules can be cleaved at the restriction site in the presence of a restriction endonuclease specific for the site and the appropriate buffer and reaction conditions to form cDNA having a promoter upstream of a coding sequence, oriented to transcribe downstream. The resulting cDNA can be in vitro transcribed using the appropriate RNA polymerase to form cRNA molecules that represent mRNA molecules that are not common to the two mRNA populations. The other manipulations described above for the basic method are also possible with the cDNA molecules, including in vitro transcription and translation, sequencing, other amplifications, and expression.

Another method of the invention is a method of reducing the quantity of particular mRNA species present in a population of mRNA, sometimes called the process of normalization or equalization of an mRNA population. This method is particularly useful for construction of template cDNA where some mRNA transcripts in the original mRNA population are more abundant than other transcripts. It is a way of equalizing the quantity of mRNA for each gene transcriptionally expressed in the cell. To practice this method, a first mRNA population is reverse transcribed using standard protocols for reverse transcription including reverse transcriptase enzyme, deoxyribonucleotide-triphosphates, and a first nucleotide primer comprising in 5' to 3' order: (i) a promoter, (ii) a restriction endonuclease cleavage site, and (iii) an oligonucleotide dT sequence having at least 10 dTs, wherein the promoter sequence is oriented so that it initiates transcription towards the 5' end, and further wherein between 0 and 100 nucleotides, or more, are between each of elements (i), (ii), and (iii), to form first strand cDNA comprising at a 5' end the first primer sequence. The mRNA is removed from the first strand cDNA as described above. Then another sample of mRNA from the same cell type or population source is hybridized to the first strand cDNA just constructed. The hybridization takes place for a monitored amount of time. The time period is selected based on the relative abundance of the mRNA to be partially eliminated. Thus, for example, where the species of mRNA to be partially eliminated is highly abundant, incubation would be allowed to proceed for a longer period of time. The period of time can range from anywhere from two hours to 48 hours. The longer the incubation, the more hybrids are formed, and the more copies of the mRNA template will be removed from the population under study. Thus, one will tailor the length of the incubation to an estimate of the relative abundance of the mRNA, which is being eliminated in the normalization process. A very abundant mRNA will need the longer incubation to remove significant amount of the abundant mRNA copies. The composition that is formed should be cDNA:mRNA hybrids that use some but not all of the cDNA newly synthesized. The hybrids are removed as described above. The hybrids can be removed by chromatography selecting for the RNA, or other means capable of selectively removing the hybrids and leaving the single stranded cDNA. Remaining in the mixture is a representation of cDNA that has been normalized so that there are less cDNA molecules in the population which represent the abundant mRNA species present in the cell or tissue population than in the initial population of mRNA isolated. The cDNA remaining is then phosphorylated, and ligated with T4 RNA ligase. From the ligation reaction the linear catenates and circular molecules described above are formed. Double stranded cDNA can be formed from using these single stranded molecules as templates. The single stranded cDNA is then used as a template as described above to form double stranded cDNA linear catenates or circular cDNA. These double stranded linear catenates or circular cDNA are cleaved with the restriction endonuclease to form double stranded cDNA templates that have been normalized to represent more equal quantities of transcripts from the population of mRNA than had been present in nature. The resulting linear double stranded cDNA has a promoter upstream of a coding sequence, oriented to transcribe downstream, and can then be used in an in vitro transcription reaction to form cRNA, in an in vitro transcription and translation reaction to form a polypeptide, can be ligated into a vector for expression or sequencing, can be sequenced from the linear template, can be further amplified by PCR or other amplification process, or can be used to perform other analysis or manipulations.

EXAMPLES

Example 1: Construction of Linear cDNA Library

Total RNA was isolated from cells or tissues using the isolation method described in Ausubel et al., CURRENT PROTOCOLS IN MOLECULAR BIOLOGY (1994), Greene Publishing Associates and John Wiley & Sons, New York, N.Y. and the pure RNA was stored at −80° C. Poly A+RNA was isolated by using a commercial kit called Quick Prep micro mRNA purification kit available from Pharmacia, Piscataway, N.J.

First strand cDNA was synthesized using 0.1 ug or more of poly A+RNA. 1.5 ul of the primer having this sequence was added. The primer comprises 5' miscellaneous nucleotides+antisense SP6 sequence+SFI I cutting site+an oligo dT sequence 3'. The sequence of the primer is as follows: 5'-CTC GTA TTC TAT AGT GTC ACC TAA ATG GCC TAT ATG GCC TTT TTT TTT TTT TTT TTT TTT TT-3' (SEQ ID NO: 1) The SP6 sequence is: ATT TAG GTG ACA CTA TAG (SEQ ID NO: 2). The sequence in the primer for the SP6 is 5'-TC TAT AGT GTC ACC TAA AT-3' (SEQ ID NO: 3) which is an antisense sequence of the SP6 sequence. The SFI I cutting site is 5'-G GCC TAT ATG GCC-3' (SEQ ID NO: 4). The primer was added, in up to 30 ul of DEPC treated water. The reaction was mixed gently, heated to 68° C. for five minutes, and cooled on ice for ten minutes. First strand cDNA was synthesized in this tube with the addition of 10 ul of 5× reverse transcription buffer, 1 ul of RNase enzyme inhibitor, 8 ul of dNTP (at a concentration of 5 mM for a final concentration of 200 uM), 1 ul of reverse transcriptase enzyme, for a total volume of 50 ul. The reaction tube contents were mixed gently and incubated at 37° C. for about 1 hour.

The RNA in the reaction was then digested by one of the following methods. One tenth volume of RNase buffer was added to an RNase H and RNase A mixture and incubated at 30° C. for one hour. Optionally, another way to remove the RNA is using NaOH. One ul of 0.5 EDTA, pH 8.0 and 12.5 ul of 0.15 N sodium hydroxide was added and the reaction incubated at 68° C. for 15 minutes. After incubation 12.5 ul of 1M Tris, pH 8.0 and 12.5 ul of 1 N hydrochloric acid were added. The first strand cDNA was extracted and precipitated by adding 1×TE up to 200 ul. This solution was extracted with phenol:chloroform and chloroform. Sodium acetate (one tenth volume of sample) was added followed by absolute ethanol (2× volume). This solution was mixed by inverting several times, and then spun in a microfuge for 20 minutes. The pellet was washed with 70% ethanol, and the remaining pellet was dried in open air.

The DNA was prepared for ligation by phosphorylating. The pellet first strand cDNA was resuspended in 40 ul of water. Five ul of the 10× kinase buffer, 1 ul of ATP and 4 ul of T4 polynucleotide kinase were mixed together and added to the DNA. The reaction was incubated at 37° C. for one hour. The phosphorylated DNA was extracted and precipitated as just described for the first strand cDNA.

For the ligation reaction, the pelleted DNA was resuspended in 10 ul of water. Two ul of 10×ligation buffer was added along with 25 ul of 40 polyethylene glycol, 2 ul of T4 RNA ligase, and the reaction was incubated overnight (or about 12 to 18 hours) at 17° C.

The resulting reaction was extracted and precipitated as described above.

Second strand cDNA was made by first suspending the resulting DNA pellet in 80 ul of water. Two ug of specific second primer complementary to the first primer was added having the following sequence: 5'-ATT TAG GTG ACA CTA TAG-3' (SEQ ID NO: 2) The reaction was mixed and incubated at 37° C. for 30 minutes. The following reagents were added: 30 ul of 5×$2^{nd}$ strand buffer, 3 ul of 10 mM dNTP, 1 ul of E. coli DNA ligase, 4 ul of E. coli DNA polymerase I, and water up to 150 ul. The reaction was mixed gently and incubated at 16° C. for 2 hours. Two ul of T4 DNA polymerase and incubated at 16° C. for 10 minutes.

The resulting DNA was extracted and precipitated as described above. The double stranded DNA was ligated by resuspending the DNA pellet in 10 ul of water. Two ul of 10× ligation buffer, and 2 ul of T4 DNA ligase were added, and the reaction was incubated overnight at 16° C. or for about 12 to 18 hours. The resulting DNA was extracted and precipitated as described above.

The DNA pellet was resuspended in 10 ul of water for the restriction endonuclease digestion. Two ul of restriction buffer M from Boehringer Mannheim, Indianapolis, Ind., were added for use in a restriction digestion with SFI I enzyme also from Boehringer Manneheim. The reaction was incubated at 37° C. for 3 hours. The resulting DNA was extracted and precipitated as described above.

cRNA was made by in vitro transcription of the resulting double stranded cDNA template. The DNA was resuspended in 9 ul of water. To this DNA solution was added 4 ul of 5× transcription buffer, 4 ul of rNTP, 1 ul of RNase inhibitor, 2 ul of SP6 RNA polymerase. These components were mixed gently and incubated at 37° C. for 2 hours. Two units of RNase free DNase was added and the reaction was incubated at 37° C. for 15 minutes.

Example 2: Alternative Construction of Linear cDNA Library

T4 RNA ligase and buffer (available from New England Bio-Labs, Inc, Beverly, Mass.) was incubated with n-RNA population, and a primer (the DNA-RNA primer) having the following sequence: 5'GAA GAT CTG GCC CAT ATG GCC A- GGA 3' (SEQ ID NO: 5) (the GGA at the 3' end were ribonucleotides) was added to the reaction mixture. The ligation conditions were 10×RNA ligase buffer (5 (1), DNA-RNA primer (5 (1), RNA inhibitor (called RNAsin, available from Promega, Inc, Madison, Wis.) 2 (1, T4 RNA ligase (5 (1), 40% polyethylene glycol (25 (1) and water up to 50 (1. The reaction was gently mixed and incubated at 17° C. for about 16 hours.

Example 3: Northern Hybridization Analysis of Amplified mRNA

Total RNA from A549 cells was isolated by standard protocol as described in Ausubel et al., CURRENT PROTOCOLS IN MOLECULAR BIOLOGY (1994), (Greene Publishing Associates and John Wiley & Sons, New York, N.Y.). Poly A+RNA was isolated from human liver. An aliquot of the poly A+RNA was subjected to the procedures described in Example 1 for amplification of mRNA. Total RNA, poly A+RNA from human liver, and amplified poly A+RNA were separated by gel electrophoresis through 1% denaturing agarose gel, transferred to a nylon membrane, and hybridized with Digitoxin labeled antisense RNA of PKC(, cRaf, and G3PDH. The Dig label was detected by monoclonal antibody against Dig conjugated with alkaline phosphatase. PKC( migrated at 8.5 kb; cRaf migrated at 3 kb, and G3PDH migrated at 1.3 kb. The relative intensities of the label for the total RNA, versus the poly A+RNA, versus the amplified poly A+RNA are as follows:

| A549 cells – 6 ug of total RNA | 1 ug poly A + RNA (human liver) before amplific. | 1 ug poly A + RNA (human liver) after amplification | |
|---|---|---|---|
| + | -- | ++++++ | PKC ((8.5 kb) |
| + | ++ | +++++ | c-Raf (3 kb) |
| + | ++ | ++++ | G3PDH (1.3 kb) |

What is claimed is:

1. A method of forming a DNA template for producing mRNA comprising the steps of:

providing a single stranded DNA molecule comprising in 5' to 3' order: (a) a promoter, (b) a restriction endonuclease cleavage site, (c) an oligonucleotide dT sequence having at least 10 dTs, and (d) a coding sequence, wherein the promoter is oriented such that it initiates transcription towards the 5' end, and further wherein between 0 and 100 nucleotides are between each of elements (a), (b), and (c);

ligating the single-stranded DNA molecule to form a linear DNA catenate comprising at least two series of elements (a), (b), (c), and (d) or a circular DNA;

providing a second strand complementary to and hydrogen-bonded to the single stranded DNA molecule to form a double-stranded linear catenate or a circular DNA molecule; and cleaving the double-stranded linear catenate or the circular DNA molecule with the restriction endonuclease to form the DNA template having a promoter upstream of the coding sequence wherein the promoter is oriented to transcribe downstream.

2. A method of forming a DNA template for producing antisense mRNA comprising the steps of:

providing a single stranded DNA molecule comprising in 5' to 3' order: (a) a restriction endonuclease cleavage site, (b) a promoter, (c) an oligonucleotide dT sequence having at least 10 dTs, and (d) a first cDNA sequence, wherein the promoter is oriented such that it initiates transcription towards the 3' end, and further wherein between 0 and 100 nucleotides are between each of elements (a), (b), and (c);

ligating the single-stranded DNA molecule to form a linear DNA catenate comprising at least two series of elements (a), (b), (c), and (d) or a circular DNA;

providing a second strand complementary to and hydrogen-bonded to the single stranded DNA molecule to form a double-stranded linear catenate or a circular DNA molecule; and cleaving the double-stranded linear catenate or a circular DNA molecule with the restriction endonuclease to form the DNA template having the promoter downstream of the coding sequence wherein the promoter is oriented to transcribe upstream.

3. A method of making cDNA comprising, (a) incubating mRNA with reverse transcriptase, deoxyribonucleotide triphosphates and a first oligonucleotide primer comprising in a 5' to 3' orientation (i) a promoter, (ii) a restriction endonuclease cleavage site, and (iii) an oligonucleotide dT sequence having at least 10 dTs, wherein the promoter is oriented so that it initiates transcription towards the 5' end, and further wherein between 0 and 100 nucleotides are between each of elements (i), (ii), and (iii) to form first strand cDNA comprising at its 5' end the first oligonucleotide primer, (b) removing the mRNA from the first strand cDNA, (c) phosphorylating the 5' end of the first strand cDNA, (d) ligating the phosphorylated first strand cDNA with ligase to form a linear catenate of first strand cDNA or a circular first strand cDNA, (e) incubating the linear catenate or circular cDNA with a DNA polymerase, deoxyribonucleotide triphosphates, and a second oligonucleotide primer which is complementary to at least 12 nucleotides of the first oligonucleotide primer to form a double stranded linear catenate or circular cDNA, (f) cleaving the double stranded linear catenate or circular cDNA with the restriction endonuclease to form a double stranded template having the promoter upstream of the cDNA, oriented to transcribe downstream.

4. The method of claim 3, further comprising, (g) transcribing the double stranded template of step (f) with RNA polymerase and nucleotide triphosphates, to form single stranded cRNA.

5. The method of claim 3, further comprising, (h) amplifying the double stranded template of step (f) with DNA polymerase, deoxyribonucleotide triphosphates, a third oligonucleotide primer complementary to at least 12 nucleotides of the 3' end of a first strand of the cDNA, and a fourth oligonucleotide, primer complementary to at least 12 nucleotides of the 3' end of the second strand.

6. The method of claim 3, further comprising (i) transcribing and translating in vitro the double stranded template of step (f) to make a polypeptide encoded by the cDNA.

7. The method of claim 3, wherein step (b) is performed using RNase or NaOH.

8. The method of claim 3, wherein the promoter is selected from the group consisting of a T7, T3 and SP6 promoter.

9. The method of claim 3, wherein the mRNA is present in a preparation of total RNA.

10. The method of claim 3, wherein the restriction endonuclease site comprises 8 nucleotides.

11. A method of making cDNA comprising, (a) decapping an mRNA, (b) ligating a first oligonucleotide primer comprising a first promoter to a 5' end of the mRNA molecule to form an RNA template, wherein the first promoter is oriented to transcribe towards the 3' end, (c) reverse transcribing the RNA template of step (b) with reverse transcriptase, deoxyribonucleotide triphosphates and a second oligonucleotide primer comprising an oligonucleotide dT sequence of at least 10 dTs, and an additional nucleotide sequence 5' of the oligonucleotide dT sequence, to form first strand cDNA, (d) removing the mRNA from the first strand cDNA, (e) incubating the first strand cDNA, a DNA polymerase, deoxyribonucleotide triphosphates, and a third oligonucleotide primer comprising at least 12 nucleotides of the first primer sequence, to form double stranded cDNA.

12. A method of making cDNA comprising, (a) decapping an mRNA, (b) ligating a first oligonucleotide primer to a 5' end of the mRNA molecule to form an RNA template, (c) reverse transcribing the RNA template of step (b) with reverse transcriptase, deoxyribonucleotide triphosphates and a second oligonucleotide primer comprising an oligonucleotide dT sequence of at least 10 dTs, and a promoter upstream of the oligonucleotide dT sequence, wherein the promoter is oriented so that it initiates transcription downstream, to form first strand cDNA, (d) removing the mRNA from the first strand cDNA, (e) incubating the first strand cDNA, a DNA polymerase, deoxyribonucleotide triphosphates, and a third oligonucleotide primer comprising at least 12 nucleotides of the first primer sequence, to form double stranded cDNA.

13. The method of claim 10, wherein the second oligonucleotide primer further comprises a second promoter upstream of the oligonucleotide dT sequence, wherein the promoter is oriented such that it initiates transcription downstream and further wherein the second promoter comprises a promoter sequence distinct from the first promoter sequence.

14. The method of claim 10, further comprising (f) transcribing the double stranded cDNA of step (e) with RNA polymerase, nucleotide triphosphates, and a primer sequence comprising a promoter, to form cRNA.

15. A method of subtractive hybridization identifying mRNA transcripts that are not common to two populations of mRNA comprising, (a) reverse transcribing a first mRNA population with reverse transcriptase, deoxyribonucleotide triphosphates, and a first nucleotide primer comprising in 5' to 3' order: (i) a promoter, (ii) a restriction endonuclease cleavage site, and (iii) an oligonucleotide dT sequence having at least 10 dTs, wherein the promoter is oriented so that it initiates transcription towards the 5' end, and further wherein between 0 and 100 nucleotides are between each of elements (i), (ii), and (iii), to form first strand cDNA comprising at a 5' end the first primer sequence, (b) removing the mRNA from the first strand cDNA, (c) hybridizing the first strand cDNA of step (b) to a second mRNA population to form a composition comprising cDNA:mRNA hybrids and nonhybridized first strand cDNA, (d) eliminating the cDNA:mRNA hybrids from the composition, (e) ligating the composition comprising nonhybridized first strand cDNA with ligase to form linear catenates or circular first strand cDNA, (f) incubating the first strand linear catenates or circular cDNA with DNA polymerase, deoxyribonucleotide triphosphates, and a second oligonucleotide primer complementary to at least 12 nucleotides of the first primer sequence to form double stranded linear catenates or circular cDNA, (g) cleaving the double stranded linear catenates or circular cDNA with the restriction endonuclease to form cDNA having a promoter upstream of a coding sequence oriented to transcribe downstream representing mRNA molecules which are not common to the two mRNA populations.

16. A method of reducing the quantity of a select mRNA present in a population of mRNA comprising, (a) reverse transcribing a first mRNA population with reverse transcriptase, deoxyribonucleotide triphosphates, and a first nucleotide primer comprising in 5' to 3' order: (i) a promoter, (ii) a restriction endonuclease cleavage site, and (iii) an oligonucleotide dT sequence having at least 10 dTs, wherein the promoter sequence is oriented so that it initiates transcription towards the 5' end, and further wherein between 0 and 100 nucleotides are between each of elements (i), (ii), and (iii), to form first strand cDNA comprising at a 5' end the first primer sequence, (b) removing the mRNA from the first strand cDNA, (c) hybridizing for a sufficient period of time the first strand cDNA of step (a) to the mRNA of step (a) to form a composition comprising cDNA:mRNA hybrids of some but not all of the cDNA and mRNA pairs that can hybridize, (d) eliminating the cDNA:mRNA hybrids that are formed from the composition, (e) ligating the composition comprising nonhybridized first strand cDNA with ligase to form linear catenates or circular first strand cDNA, (f) incubating the first strand linear catenates or circular cDNA with DNA polymerase, deoxyribonucleotide triphosphates, and a second oligonucleotide primer complementary to at least 12 nucleotides of the first primer sequence to form double stranded linear catenates or circular cDNA, (g) cleaving the double stranded linear catenates or circular cDNA with the restriction endonuclease to form cDNA having a promoter upstream of a coding sequence, oriented to transcribe downstream, representing mRNA molecules that are not common to the two mRNA populations.

17. The method of claim 16, wherein step (c) comprises an incubation ranging from 2 hours to 48 hours.

* * * * *